US005720832A

United States Patent [19]

Minto et al.

[11] Patent Number: 5,720,832
[45] Date of Patent: Feb. 24, 1998

[54] METHOD OF MAKING A MELTBLOWN NONWOVEN WEB CONTAINING ABSORBENT PARTICLES

[75] Inventors: Mansoor Ahmad Minto, Larkfield; Dennis Graham Storey, Bearsted; Geoffrey Robert Owen, Ditton, all of Great Britain

[73] Assignee: Kimberly-Clark Ltd., Kent, England

[21] Appl. No.: 471,088

[22] Filed: Jun. 6, 1995

Related U.S. Application Data

[62] Division of Ser. No. 71,048, Jun. 1, 1993, which is a continuation of Ser. No. 787,708, Oct. 16, 1985, abandoned, which is a continuation of Ser. No. 530,600, filed as PCT/GB82/00334, published as WO11/24/82, abandoned.

[30] Foreign Application Priority Data

Nov. 24, 1981 [GB] United Kingdom ............... 8135331

[51] Int. Cl.⁶ ..................................................... D04H 1/54
[52] U.S. Cl. ........................... 156/62.4; 442/400; 442/417
[58] Field of Search ....................... 156/62.4; 442/400, 442/417

[56] References Cited

U.S. PATENT DOCUMENTS

| Re. 31,323 | 7/1983 | Marder et al. ............... 536/87 |
| 2,394,657 | 2/1946 | Beregh ....................... 91/18 |
| 2,464,301 | 3/1949 | Francis . |
| 2,810,716 | 10/1957 | Markus . |
| 2,881,769 | 4/1959 | Touey ....................... 131/208 |
| 2,917,054 | 12/1959 | Touey ....................... 131/208 |
| 2,988,469 | 6/1961 | Watson . |
| 3,008,472 | 11/1961 | Touey ....................... 131/208 |
| 3,016,599 | 1/1962 | Perry ....................... 28/78 |
| 3,221,938 | 12/1965 | Yonkers et al. ............. 222/76 |
| 3,273,016 | 9/1966 | Buhler ....................... 317/3 |
| 3,292,045 | 12/1966 | Buhler ....................... 317/3 |
| 3,292,046 | 12/1966 | Buhler ....................... 317/3 |
| 3,336,149 | 8/1967 | Fox et al. . |
| 3,341,740 | 9/1967 | Buhler ....................... 317/2 |
| 3,344,312 | 9/1967 | Buhler ....................... 317/2 |
| 3,359,224 | 12/1967 | Faessinger et al. . |
| 3,425,971 | 2/1969 | Gugliemelli et al. . |
| 3,542,708 | 11/1970 | Douglas et al. . |
| 3,571,659 | 3/1971 | Van Turnhout ............. 317/262 |
| 3,589,364 | 6/1971 | Dean et al. ................. 128/284 |
| 3,661,302 | 5/1972 | Braun ....................... 222/226 |
| 3,669,103 | 6/1972 | Harper et al. . |
| 3,670,731 | 6/1972 | Harmon . |
| 3,676,242 | 7/1972 | Prentice ................... 156/62.4 |
| 3,678,031 | 7/1972 | Schoggen . |
| 3,680,779 | 8/1972 | Reilly ....................... 239/3 |
| 3,760,990 | 9/1973 | Lindquist ................... 222/371 |
| 3,779,800 | 12/1973 | Heiser . |
| 3,793,678 | 2/1974 | Appel ....................... 19/156.3 |
| 3,823,057 | 7/1974 | Roberts et al. . |
| 3,888,207 | 6/1975 | Stutz et al. ................ 118/621 |
| 3,935,099 | 1/1976 | Weaver et al. . |
| 3,935,363 | 1/1976 | Burkholder et al. ......... 428/281 |
| 3,960,323 | 6/1976 | Ducan et al. ............... 239/3 |
| 3,971,373 | 7/1976 | Braun ....................... 428/328 |
| 3,981,100 | 9/1976 | Weaver et al. ............. 47/58 |
| 3,984,361 | 10/1976 | Gugliemelli et al. . |
| 3,993,553 | 11/1976 | Assarsson et al. . |
| 3,997,484 | 12/1976 | Weaver et al. . |
| 3,998,988 | 12/1976 | Shimomai et al. .......... 428/400 |
| 4,011,067 | 3/1977 | Carey ....................... 55/354 |
| 4,042,971 | 8/1977 | Brennecke et al. ......... 361/213 |
| 4,043,952 | 8/1977 | Ganslaw et al. . |
| 4,056,103 | 11/1977 | Kaczmarzyk et al. . |
| 4,060,648 | 11/1977 | Taylor-Brown et al. ..... 427/32 |
| 4,071,169 | 1/1978 | Dunn ....................... 222/76 |
| 4,082,516 | 4/1978 | Metzger ................... 44/51 |
| 4,088,726 | 5/1978 | Cumbers ................... 264/123 |
| 4,099,218 | 7/1978 | Klein et al. ................ 361/433 |
| 4,100,324 | 7/1978 | Anderson et al. .......... 428/288 |
| 4,103,058 | 7/1978 | Humlicek ................. 428/171 |
| 4,103,062 | 7/1978 | Aberson et al. ........... 428/283 |
| 4,105,033 | 8/1978 | Chatterjee et al. . |
| 4,116,899 | 9/1978 | Fanta et al. . |
| 4,118,531 | 10/1978 | Hauser ..................... 428/224 |
| 4,123,397 | 10/1978 | Jones . |
| 4,124,875 | 11/1978 | Van Zantwyk ............ 361/227 |
| 4,128,692 | 12/1978 | Reid ....................... 428/378 |

(List continued on next page.)

FOREIGN PATENT DOCUMENTS

| 1527536 | 4/1968 | France . |
| 1253117 | 10/1967 | Germany . |
| 2453139 | 5/1975 | Germany . |
| 2615325 | 11/1976 | Germany . |
| 2737941 | 3/1978 | Germany . |
| 2741178 | 3/1978 | Germany . |
| 56-6097 U | 2/1981 | Japan . |
| 568574 | 4/1945 | United Kingdom . |
| 883108 | 11/1961 | United Kingdom . |

(List continued on next page.)

OTHER PUBLICATIONS (Anon.), "Superabsorbents Seek Markets that are Super", Chemical Week 40 (Jul. 18, 1979).

Bagley, E.B. et al., "Starch–Polyacrylonitrile Copolymers. Properties of Hydrogels", Ind. Eng. Chem., Prod. Res. Dev., 14(2), 105–07 (1975).

Buntin, R.R. et al., "Melt Blowing—A One Step Process for New Nonwoven Products", TAPPI 56, 74–77 (1973).

(List continued on next page.)

Primary Examiner—James C. Cannon
Attorney, Agent, or Firm—Brinks Hofer Gilson & Lione

[57] ABSTRACT

A method of making a non-woven web of melt blown polymeric fibers wherein the melt blown fibers have particles introduced into the stream of microfibers after the microfibers have been extruded. If the particles are of super absorbent material they are distributed substantially individually and spaced throughout the web and provide effective results when used for example in a sanitary napkin, diaper or incontinence pad. If the particles are for example, clay, calcium carbonate, kaolin chalk or the like, then a wiper product made from the web has improved wiping properties.

11 Claims, 10 Drawing Sheets

U.S. PATENT DOCUMENTS

| | | | |
|---|---|---|---|
| 4,134,862 | 1/1979 | Eden et al. | |
| 4,134,863 | 1/1979 | Fanta et al. | |
| 4,146,177 | 3/1979 | Jordan et al. | 239/15 |
| 4,153,421 | 5/1979 | Marlin | 44/51 |
| 4,156,664 | 5/1979 | Skinner et al. | |
| 4,159,260 | 6/1979 | Jones et al. | |
| 4,160,059 | 7/1979 | Samejima | 428/28 |
| 4,172,058 | 10/1979 | Hall . | |
| 4,174,417 | 11/1979 | Rydell | 428/221 |
| 4,186,165 | 1/1980 | Aberson et al. | 264/112 |
| 4,192,785 | 3/1980 | Chen et al. | |
| 4,195,634 | 4/1980 | DiSalvo et al. | |
| 4,200,736 | 4/1980 | Shinohara et al. | 536/87 |
| 4,200,737 | 4/1980 | Marder et al. | 536/87 |
| 4,211,816 | 7/1980 | Booker et al. | 428/298 |
| 4,215,682 | 8/1980 | Kubik et al. | 128/205.29 |
| 4,235,237 | 11/1980 | Mesek et al. | |
| 4,252,761 | 2/1981 | Schoggen et al. | 264/120 |
| 4,255,777 | 3/1981 | Kelly | 361/228 |
| 4,295,987 | 10/1981 | Parks | 252/194 |
| 4,297,410 | 10/1981 | Tsuchiya et al. | 428/283 |
| 4,298,668 | 11/1981 | Schmidt et al. | 429/250 |
| 4,321,161 | 3/1982 | Watenabe et al. | 252/440 |
| 4,335,722 | 6/1982 | Jackson . | |
| 4,354,901 | 10/1982 | Kopolow | 162/158 |
| 4,372,312 | 2/1983 | Fendler et al. | |
| 4,429,001 | 1/1984 | Kolpin et al. | 428/283 |
| 4,469,734 | 9/1984 | Minto et al. | 428/134 |
| 4,664,816 | 5/1987 | Walker . | |
| 4,689,408 | 8/1987 | Gelman et al. | 536/98 |
| 4,743,440 | 5/1988 | Callingham et al. | 424/46 |
| 4,755,178 | 7/1988 | Insley et al. | 604/367 |
| 4,773,903 | 9/1988 | Weisman et al. | 604/368 |
| 4,795,453 | 1/1989 | Wolfe | 604/385.1 |
| 4,822,596 | 4/1989 | Callingham et al. | 424/46 |

FOREIGN PATENT DOCUMENTS

| | | |
|---|---|---|
| 953709 | 3/1964 | United Kingdom . |
| 1079275 | 8/1967 | United Kingdom . |
| 1088293 | 10/1967 | United Kingdom . |
| 1234075 | 6/1971 | United Kingdom . |
| 1295267 | 11/1972 | United Kingdom . |
| 1441711 | 7/1976 | United Kingdom . |
| 1493183 | 11/1977 | United Kingdom . |
| 1522605 | 8/1978 | United Kingdom . |
| 1527592 | 10/1978 | United Kingdom . |
| 2006614 | 5/1979 | United Kingdom . |
| 2015253 | 9/1979 | United Kingdom . |
| 2020086 | 11/1979 | United Kingdom . |
| 1564575 | 4/1980 | United Kingdom . |
| 2034604 | 6/1980 | United Kingdom . |
| 2039304 | 8/1980 | United Kingdom . |
| 1579568 | 11/1980 | United Kingdom . |
| 1581486 | 12/1980 | United Kingdom . |
| 2060018 | 4/1981 | United Kingdom . |
| 1591415 | 6/1981 | United Kingdom . |
| 2112828 | 7/1983 | United Kingdom . |
| 2113731 | 8/1983 | United Kingdom . |
| 2151272 | 7/1985 | United Kingdom . |
| WO 83/01965 | 6/1983 | WIPO . |

OTHER PUBLICATIONS

Burr, R.C. et al., "Influence of Swelling and Disruption of the Starch Granule on the Composition of the Starch–Polyacrylonitrile Copolymer", J. Macromol. Sci.—Chem. A1(7) 1381–85 (1967).

Burr, R.C. et al., "Copolymers of Wheat Starch and Polyacrylonitrile. Effect of Aqueous—Organic Solvent Systems on Copolymer Composition", J. Macromol. Sci.—Chem. A2(1), 93–101 (1968).

Chatterjee, P.K., ed., Absorbency, 211–16 and 257–58 (1985).

Dennenberg, R.J. et al., "Rapid Analysis of Starch Graft Copolymers", J. Polym. Sci., Polym. Lett. Ed., 14(11), 693–96 (1976).

Erickson, R.E., First International Absorbent Products Conference Proceedings, Insight 80 (Nov. 19–21, 1980), Section VI, pp."Section VI–1" to Section VI–15 and Section VI–19 to Section VI–24.

Fanta, G.F. et al., "Copolymers of Starch and Polyacrylonitrile. Influence of Granule Swelling on Copolymer Composition under Various Reaction Conditions", J. Macromol. Sci.—Chem. A4(2), 331–39 (1970).

Fanta, G.F. et al., "Graft Copolymers of Starch. II. Copolymerization of Wheat Starch with Acrylonitrile: Influence of Reaction Conditions on Copolymer Composition", J. Polym. Sci., Polym. Lett. Ed., 4(10), 765–69 (1966).

Flory, P.J., Principles of Polymer Chemistry, 584–89 (1953).

Gugliemelli, L.A. et al., "Base–Hydrolyzed Starch–Polyacrylonitrile (S–PAN) Graft Copolymer. S–PAN–1, Pan M.W. 794,000", J. Appl. Polym. Sci. 13(9), 2007–17 (1969).

Gugliemelli, L.A. et al., "Kinetics of Grafting Acrylonitrile onto Starch", J. Polym. Sci., Polym. Chem. Ed., 11(10), 2415–62 (1973).

Guyon, J., "Super Slurper Mops Flood of Possibilities in Quest for Markets", Wall Street Journal, 22, col. 3 and 4 (Mar. 3, 1980).

Kern, W. "Ueber die Polymerisation der monomeren akrylsaeure zu loeslichen und unloeslichen Polymeren" (The Polymerization of Monomeric Acrylic Acid to Soluble and Insoluble Polymers), Kunstoffe, 28, 257–59 (1938). (Translation provided).

Lindsay, W.F., "Absorbent Starch Based Co–polymers Their Characteristics and Applications", Nonwoven Technol.: Merging Mult Technol., Symp. Pap., Tech. Symp., 72–80 (1977).

Lindsay, W.F., "Absorbent Starch Co–polymers", TAPPI Annual Meeting Preprints, 203–05 (1977).

Lindsay, W.F., "Absorbent Starch Co–polymers", TAPPI Pap. Synth. Conf. Prepr., 37–41 (1975).

Nagaty, A. et al., "Starch and Polymer as Beater Additives", Indian Pulp Pap., 33(3), 5–7, 9–14 (1978).

Maher, G.G., "Grafting Starch Xanthate with Vinyl Monomers and Hydrogen Peroxide in Foam Rubber Production", J. Appl. Polym. Sci. 24(1), 9–17 (1979).

Mehrotra, R. et al., "Graft Copolymerization Onto Starch. II. Grafting of Acrylonitrile to Granular Native Potato Starch by Manganic Pyrophosphate Initiation. Effect of Reaction Conditions on Grafting Parameters", J. Appl. Polym. Sci. 21(12), 3407–15 (1977).

Mehrotra, R. et al., "Graft Copolymerization onto Starch. III. Grafting of Acrylonitrile to Gelatinized Potato Starch by Manganic Pyrophosphate Initiation", J. Appl. Polym. Sci. 22(10), 2991–3001 (1978).

Naval Research Laboratory Report 111,437, *Manufacture of Superfine Organic Fibers* (1954).

Otey, F.H. et al., "Starch Graft Copolymers—Degradable Fillers for Poly(vinyl chloride) Plastics", Ind. Eng. Chem., Prod. Res. Dev., 15(2), 139–42 (1976).

Oxy–Dry Corporation, undated brochure entitled, "The very best way to Solve Offset Problems is with an Oxy–Dry Sprayer System".

Ranby, B., "Methods for Graft Copolymerization onto Cellulose and Starch", Modif. Cellul., (Symp. Cellul., Pap., Text. Div. Am. Chem. Soc.) (1977 Meeting), 171–95 (1978).

The Random House Dictionary of the English Language, Second Edition Unabridged (1987), p. 1907.

Reyes, Z. et al., "Continuous Production of Acrylonitrile–Starch Graft Copolymers by Ceric Ion Catalysis", Ind. Eng. Chem., Process Des. Develop., 12(1), 62–67 (1973).

Srivastava, B.K. et al., "A New Method for Determination of Percentage Grafting in Starch–Polyacrylonitrile Graft Copolymer", Indian J. Chem., Sect. A, 14A(4), 274–75 (1976).

Stout, E.I. et al., "Graft Copolymers of Starch–Polyacrylonitrile Prpared by Ferrous Ion–Hydrogen Peroxide Initiation", J. Appl. Polym. Sci. 21(9), 2565–73 (1977).

Taylor, N.W. et al., "Tailoring Closely Packed Gel–Particle Systems for Use as Thickening Agents", J. Appl. Polym. Sci. 21(1), 113–22 (1977).

Taylor, N.W. et al., "Swelling and Rheology of Saponified Starch–g–Polyacrylonitrile Copolymers. Effect of Starch Granule Pretreatment and Grafted Chain Length", J. Appl. Polym. Sci. 22(5), 1343–57 (1978).

Taylor, N.W. et al., "Rheology of Dispersions of Swollen Gel Particles", J. Polym. Sci., Polym. Phys. Ed., 13(6), 1133–44 (1975).

U.S. Department of Agriculture, Agricultural Research Service, "Super Slurper, Compound with a Super Thirst", 4 pages (reprinted from *Agricultural Research* (Jun. 1975).

Wente, V.A., "Superfine Thermoplastic Fibers", Ind. Eng. Chem. 48, 1342–46 (1956).

Worthy, W., "Super Slurper Gaining Commercial Application", Chemical & Engineering News 23–24 (Nov. 5, 1979).

*Chem. Abstr.* 88(25), 189–140b (1978), abstract of Eikhof et al., German Patent Application 2,737,941, publishefd Mar. 9, 1978.

*Chem. Abstr.* 67(2), 3978u (1967), abstract of Fanta, G.F. et al., J. Appl. Polym. Sci., 11(3), 457–63 (1967).

*Chem. Abstr.* 79(16), 93,701y (1973), abstract of Fanta, G.F. et al., Staerke, 25(5), 157–61 (1973).

*Chem. Abstr.* 88(8), 52,231n (1978), abstract of Fanta, G.F. et al., Staerke, 29(11), 386–91 (1977).

*Chem. Abstr.* 89(14), 111,606j (1978), abstract of Fanta, G.F. et al., Staerke, 30(7), 237–42 (1978).

*Chem. Abstr.* 90(26), 206,226v (1979), abstract of Hebeish, A. et al., Angew. Makromol. Chem. 78, 101–18 (1979).

*Chem. Abstr.* 88(15), 103,671r, abstract of Leppla, N.C., J. Ga. Entomol. Soc., 11(3), 251–54 (1976).

*Chem. Abstr.* 88(24), 170,985j (1978), abstract of Lin, Chen–Chong et al., J. Chin. Inst. Chem. Eng., 8(2), 149–54 (1977).

*Chem. Abstr.* 82(10), 60,396m (1975), abstract of Nakao, T. et al., Japanese Patent Publication 74/04,555, published Feb. 1, 1974 (Application No. 70/53,284, filed Jun. 19, 1970).

*Chem. Abstr.* 83(22),181,406u (1975), abstract of Wolf, F. et al., Staerke, 27(9), 293–95 (1975).

ICCL/12-80/C
face 5,500X
(1cm=1.82microns)

ICCL/12-80/C
face 18,000X
(1cm=0.56microns)

ICCL/12-80/D
face 550X
(1cm=18microns)

METHOD OF MAKING A MELTBLOWN NONWOVEN WEB CONTAINING ABSORBENT PARTICLES

This is a division of Ser. No. 08/071,048, filed Jun. 1, 1993; which is a continuation of Ser. No. 06/787,708, filed Oct. 16, 1985, and now abandoned; which is a continuation of Ser. No. 06/530,600, filed as PCT/GB82/00334 Nov. 24, 1982, and now abandoned.

This invention relates to non-woven fabrics and in particular to those comprising a matrix of melt blown polymer fibres and a method of producing these.

Fabric made from melt blown polymer fibre is well known and is described for example in British Patent No. 2,006,614, British Patent No. 1,295,267 and U.S. Pat. No. 3,676,242. Such a fabric will be referred to hereafter as M.B.P.F.

Fabric of melt blown polyolefin fibres is useful as wiping cloths for oil and when this is additionally treated with a wetting agent, as proposed in British Patent No. 2,006,614 it has excellent oil and water wiping properties. When the fabric is also treated by a pattern bonding process it is strong and durable. However, such fabric is relatively expensive when compared with disposable wipers derived from creped tissue or paper.

It is also known to treat M.B.P.F. to make it suitable for use as a filter. This is done by incorporating particles such as activated carbon or alumina without the use of binders, by intermixing with the fibres. The particles are retained by mechanical entanglement with the fibres and do not adhere to the microfibres. Such material is unsuitable for use as a wiper since the particles are not sufficiently well retained and would tend to "dust out" or drop out of the material if used as a wiper.

A non-woven fabric in accordance with this invention comprises melt blown thermoplastic (preferably polymeric) microfibres and absorbent particles or granules, the particles or granules being firmly adhered to the fibres by being brought into contact with the fibres whilst the fibres are still in a tacky condition.

A method of making a non-woven fabric in accordance with the invention comprises extruding a molten polymeric material to produce a stream of melt blown microfibres and directing absorbent particles into the stream whilst the fibres are tacky so that the particles adhere to the fibres subsequently quenching the fibres or otherwise allowing the fibres to cool, and then forming or consolidating the fibres into a mat.

The particles in the resulting fabric web are held firmly even if the fabric is abraded or torn when used as a wiper.

The particles are preferably blown onto the stream of particles shortly after the fibres leave an extrusion nozzle and the particles may be given an electrostatic charge prior to contacting the fibres which helps to separate the particles in the web.

Other fibres such as wood pulp fibres or staple textile fibres (e.g. cotton) may also be introduced preferably simultaneously with the absorbent particles.

Preferably the fibres of the M.B.P.F. have a diameter between 1 and 50 microns, with most fibres preferably less than 10 microns. The fibres may, for example, be of polyester, polypropylene or nylon.

A wetting agent may be added to improve the water absorbency properties.

The particles, when the fabric is to be used, for example, as an industrial or catering wiper may be of a wide range of low cost absorbent granular materials such as clay, kaolin talc, calcium carbonate, sodium sulphate, sodium carbonate or aluminium oxide. It is also possible to use granular organic materials such as sponge particles. Calcined clay, particularly calcined china clay, is very useful. This has a crystalline structure and produces granules normally hollow, which are more absorbent than other clay material.

The particles may be relatively small, e.g. 1 micron or less up to 100 microns or larger and may be incorporated as individual particles or as clusters.

Particles of super absorbent material are very preferably employed to produce a web characterised by the presence of the super absorbent particles which are distributed substantially individually and spaced throughout the web.

Particulate super absorbent material (e.g. modified starch or cellulose or alginate) when added to the molten melt blown microfibres produces a web with significant unexpected benefits. The resultant web utilises the excellent wicking properties of melt blown microfibres, i.e. the high capilliary attraction present between microfibres, to rapidly convey fluid to the finely dispersed individual super absorbent particles. This isolation of the individual particles can imbibe fluid without substantial interference from gel blocking. Isolation may, for example, be produced by giving the particles an electrostatic charge before feeding them into the stream of fibres.

Gel blocking occurs when a mass of super absorbent swells upon imbibation. This swelling acts to substantially diminish the size of the capillaries in the super absorbent mass and may, in fact, close them. While other attempts at providing maximum surface per weight have been utilised, none have utilised individual isolated super absorbent particles in combination with melt blown microfibres to provide this superior wicking in combination with absorbent efficiency.

During imbibation the entire microfibre super absorbent composite swells but there is still isolation of individual particles of super absorbent. Therefore, while swelling occurs, gel blocking does not. This is true even at high levels of super absorbent addition to the composite and in fact a proportional increase in capacity and horizontal wicking is observed.

The particles of super absorbent material have relatively large diameter compared to the diameter of the individual microfibres and thus tend to be trapped within a network of the fibres and therefore little surface tack of the fibres is needed to maintain the super absorbent particles in place.

Webs with super absorbent particles may, for example, be used in sanitary napkins, diapers, incontinence pads or the like.

The particle size in one embodiment of the invention, using calcined china clay is 25% less than 2 microns, 28% greater than 10 microns and 3% greater than 20 microns. In this embodiment the clay was incorporated in a melt blown matrix of polypropylene at levels of approximately 6% and 14% and at a basis weight of approximately 90 g/m$^2$. It is considered that the particle size range should be between 1 and 100 microns with amounts of calcined clay of 5 to 40%. An increase of clay over 40% may tend to weaken the resultant product whilst not appreciably increasing the absorption capacity for water and/or oil.

It has been found that the clay particle additive significantly decreases the product cost by reducing the polymer content required per weight of the product.

The oil (SAE 10) absorptive capacity of the product with clay particles was found to be 1 to 2 grams of oil per gram of calcined clay.

In order to increase its strength, M.B.P.F. in accordance with the invention may be hot calendered or embossed with heated patterned bonding rolls. The fabric may also be perforated as described and claimed in our co-pending British Application No. 8135330 filed simultaneously herewith. This further improves the absorbency and wiping properties of the fabric.

The invention will now be further described by way of example with reference to the accompanying drawings in which.

Figure 1:
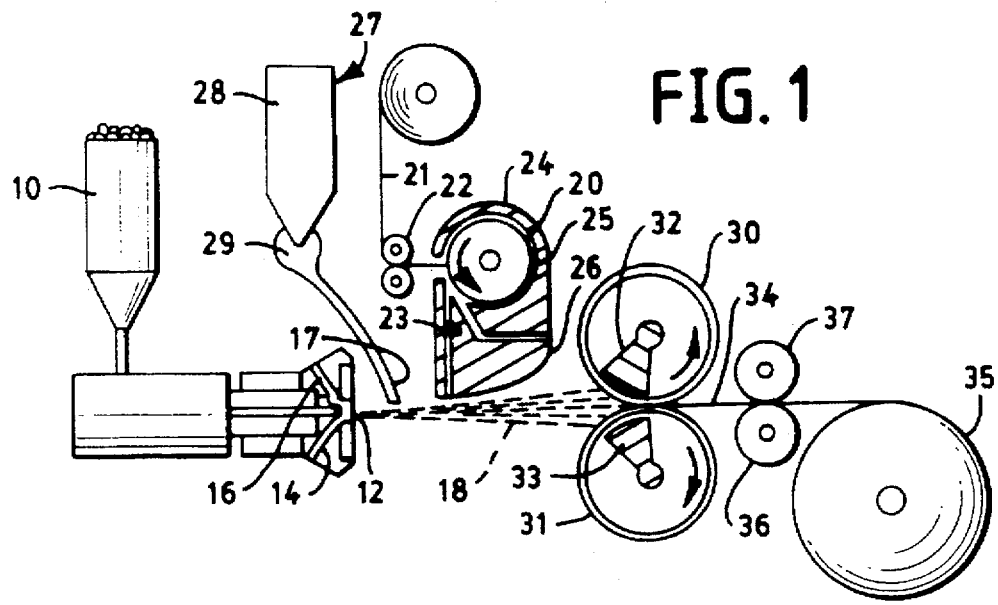
FIG. 1 is a partly schematic side elevation of an apparatus for producing fabrics according to the present invention.

Referring to FIG. 1, discontinuous thermoplastic polymeric material from a hopper 10 is heated and then caused to flow through nozzle 12 whilst being subjected to air jets through nozzles 14, 16 which produces a final stream 18 containing discontinuous microfibres of the polymeric material. This is known as melt-blowing and the technique is further described in an article entitled "Superfine Thermoplastic Fibres" appearing in Industrial and Engineering Chemistry, Vol. 48, No. 8, pp 1342–1346 which describes work done at the Naval Research Laboratories in Washington D.C. Also see Naval Research Laboratory Report No. 11437 dated 15th Apr. 1954, U.S. Pat. No. 3,676,242 and U.S. Pat. No. 4,100,324 issued to Anderson et al.

The apparatus shown in FIG. 1 is generally the same as described in U.S. Pat. No. 4,100,324 with the exception of two particular features which will be described hereinafter and the subject matter of that patent is to be considered as being included in the present specification and will not be further described. The subject matter of U.S. Pat. No. 3,793,678 entitled "Pulp Picking Apparatus with Improved Fibre Forming Duct" is also to be considered as being included in the present specification insofar as the picker roll 20 and feed 21 to 26 are concerned, as also described in U.S. Pat. No. 4,100,324.

The picker roll 20 and associated feed 21 to 26 are an optional feature of the apparatus of FIG. 1 and are provided to enable the introduction of fibrous material into the web of the invention if this is required.

The picker device comprises a conventional picker roll 20 having picking teeth for divellicating pulp sheets 21 into individual fibres. The pulp sheets 21 are fed radially, i.e., along a picker roll radius, to the picker roll 20 by means of rolls 22. As the teeth on the picker roll 20 divellicate the pulp sheets 21 into individual fibres, the resulting separated fibres are conveyed downwardly toward the primary air stream through a forming nozzle or duct 23. A housing 24 encloses the picker roll 20 and provides a passage 25 between the housing 24 and the picker roll surface. Process air is supplied to the picker roll in the passage 25 via duct 26 in sufficient quantity to serve as a medium for conveying the fibres through the forming duct 23 at a velocity approaching that of the picker teeth. The air may be supplied by any conventional means as, for example, a blower.

It has been found that, in order to avoid fibre floccing, the individual fibres should be conveyed through the duct 23 at substantially the same velocity at which they leave the picker teeth after separation from the pulp sheets 21, i.e., the fibres should maintain their velocity in both magnitude and direction from the point where they leave the picker teeth. More particularly, the velocity of the fibres separated from the pulp sheets 21 preferably does not change by more than about 20% in the duct 23. This is in contrast with other forming apparatus in which, due to flow separation, fibres do not travel in an ordered manner from the picker and, consequently, fibre velocities change as much as 100% or more during conveyance.

Further details of the picker device may be found in U.S. Pat. No. 4,100,324. The particular differences between the apparatus shown in FIG. 1 of the present specification and that of FIG. 1 of U.S. Pat. No. 4,100,324 is the means 27 for introducing particulate absorbent material into the melt blown fibre stream 18. The particle introduction means comprises a hopper 28 and air impeller 29 so arranged that the particles are ejected as a stream through a nozzle 17 into the fibre mat shortly after the nozzle 12 and whilst the melt blown fibres remain unset and tacky. The particles stick to the tacky fibres and are distributed throughout the fibre mat.

The fibres then cool as they continue in their path and/or they may be quenched with an air or water jet to aid cooling so that the fibres are set, with the particles adhered to them, before the fibres are formed into a web as described hereafter.

It is also possible to introduce the absorbent particles through the picker roll 20 and nozzle 23 either as an independent stream of particles or together with a stream of wood pulp fibres or a stream of staple textile fibres.

The hot air forming the melt blown fibres is at similar pressures and temperatures to that disclosed in U.S. Pat. No. 4,100,324.

The set fibres and particles are condensed into a web by passing the mat of fibres between rolls 30 and 31 having foraminous surfaces that rotate continuously over a pair of fixed vacuum nozzles 32 and 33. As the integrated stream 18 enters the nip of the rolls 30 and 31, the carrying gas is sucked into the two vacuum nozzles 32 and 33 while the fibre blend is supported and slightly compressed by the opposed surfaces of the two rolls 30 and 31. This forms an integrated, self-supporting fibrous web 34 that has sufficient integrity to permit it to be withdrawn from the vacuum roll nip and conveyed to a wind-up roll 35.

Alternatively, the web may be formed on a moving wire screen. The web is then further processed and bonded by hot calendering, embossing or perforating, or by ultrasonic embossing.

Heated embossing rolls 36 and 37 are provided as more fully described in our co-pending British Application No. 8135330. These rolls are driven at different speeds and the consolidated fibre web is passed between the rolls to emboss the web and bond it. The differential speed of the rolls causes the relatively outer fibres to be in effect lifted or "brushed up" giving an enhanced thickness to the web.

The embossments on the roll may extend further from the roll surface than the thickness of the web which also aids in achieving an enhanced web product.

Figure 2:
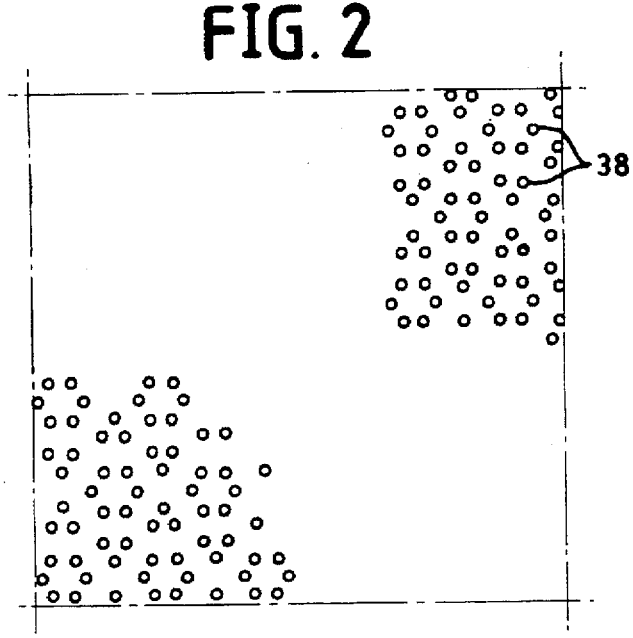
FIG. 2 is a plan view of a fragment of fabric according to the present invention which has been embossed.
Figure 3:
FIG. 3 is a cross-section of one form of embossment in the fabric of FIG. 1.

Fabrics made with the apparatus shown in FIG. 1 and with the apparatus shown but with the embossing head 40 and anvil roll 41 of U.S. Pat. No. 4,100,324 replacing rolls 36 and 37 are shown in FIG. 2, with the embossment indicated at 38 (see also FIG. 3).

Figure 4:
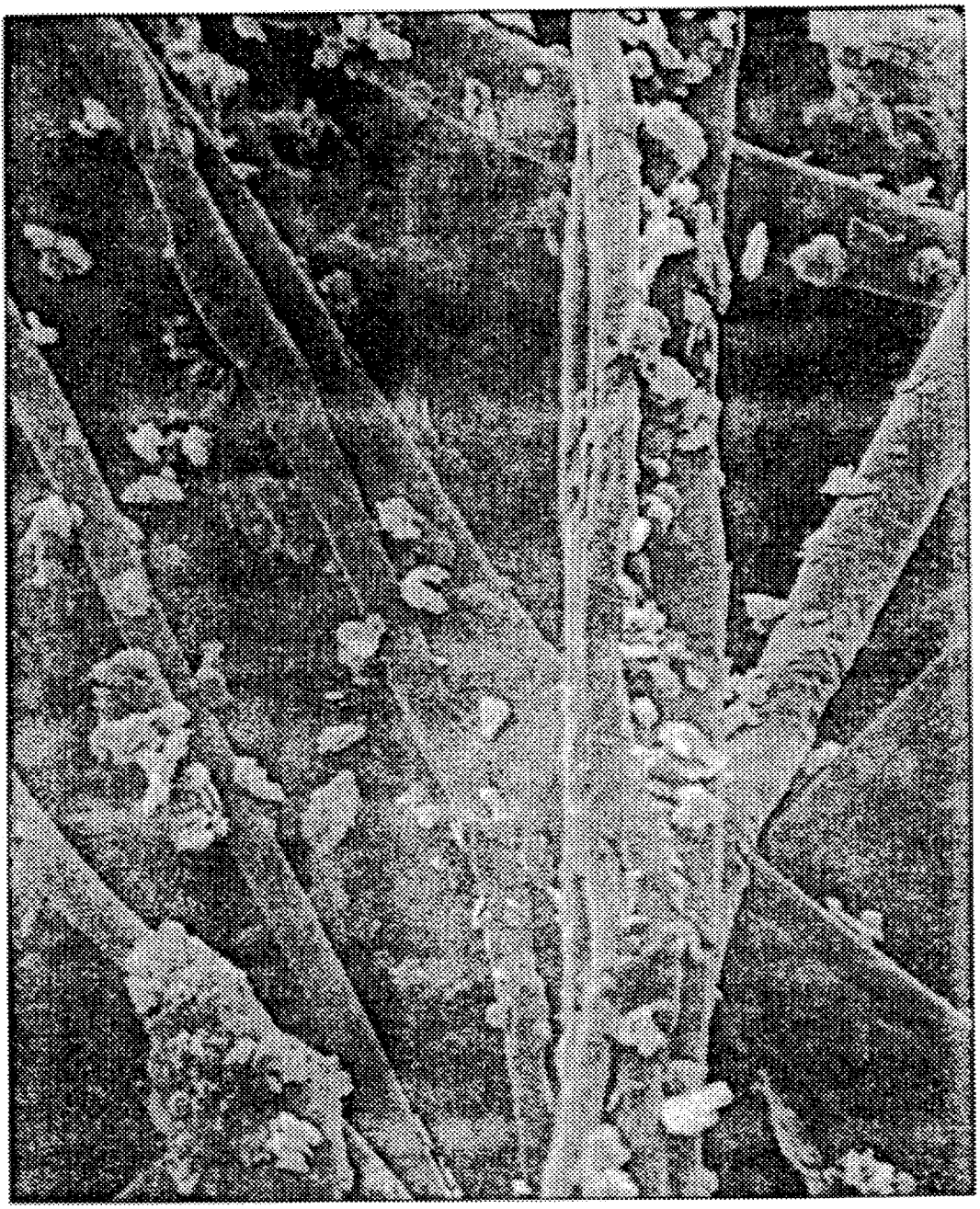
FIGS. 4 and 5 are electron microscope photographs of clay filled fabric of the present invention taken with a magnification of 5500 and 18,000 times.
Figure 5:
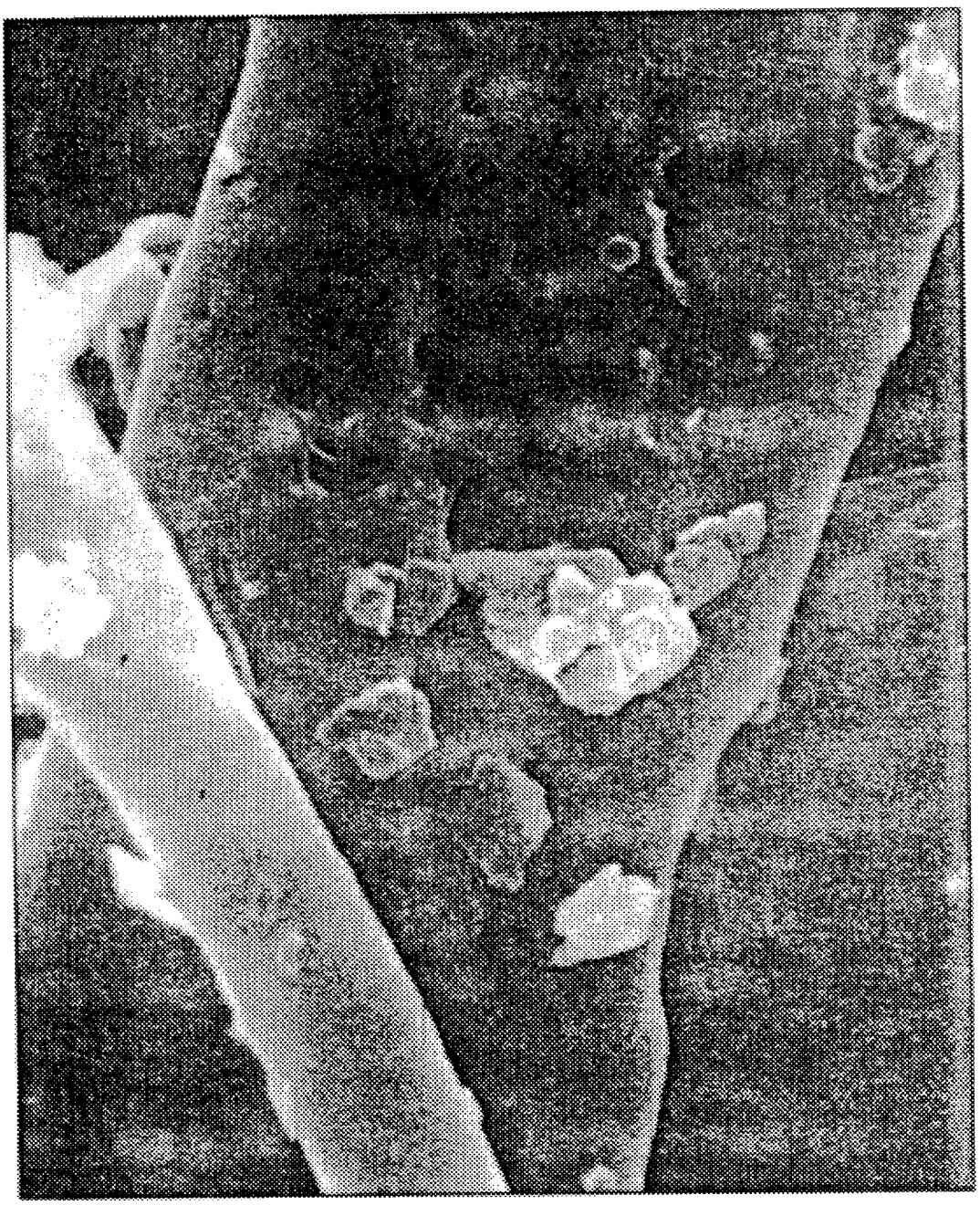
Figure 6:
FIG. 6 is an electron microscope photograph of a fabric having cellulose sponge particles.

The primary feature of the invention is the inclusion of particulate material into the M.B.P.F. This is achieved by directing the particles through a nozzle into the stream of microfibres as they leave the die head, whilst the microfibres are still tacky and the particles adhere to the microfibres or even become partially embedded in them. FIGS. 4 to 6 clearly show that the particles are adhering to the microfibres or have become partially embedded in the fibres.

One preferred particulate material is calcined English China Clay, samples of which are listed below in Table 1.

TABLE 1

| Clay Samples No. | Source | Clay Code |
|---|---|---|
| 1 | Laporte Industries Ltd., Luton, Beds. | SKY22/44 (S) |
| 2 | BDH Chemicals Ltd. Poole, Dorset. | 33058 |
| 3 | English China Clay International, St. Austell, Cornwall. | ar-501 |
| 4 | English China Clay International, St. Austell, Cornwall. | M-100 |
| 5 | English China Clay International, St. Austell, Cornwall. | Superfill |
| 6 | English China Clay International, St. Austell, Cornwall. | SPS |
| 7 | English China Clay International, St. Austell, Cornwall. | ECR |
| 8 | English China Clay International, St. Austell, Cornwall. | AlBP |

Other European clays, particularly Spanish and Italian clays, may be used.

Other particulate material such as talc, calcium carbonate, sodium sulphate, kaolin, calcium sulphate, sodium carbonate, aluminium oxide or silica may be used.

Screening studies of the clays listed in Table 1 for fluid holding capacity, rate of wickability and bulk density are given in Tables 2, 3 and 4 respectively. The Tables are set out at the end of this specification.

A comparative study of results in Table 2 shows that for water fluid holding capacity (gram/gram) Clay No. 1 is the best followed by Clay No. 5. The remaining clays performed reasonably well except Clay Nos. 3 and 4. The poor performance of these could be attributed to the fact that the particle size is well below the optimal required for water, very fine particles were lost during use, and the void volume is low. The particles size in Clay Nos. 3 and 4 were generally 20% less than 1 micron, 50% less than 2 microns and 10% greater than 10 microns.

On the other hand the oil (SAE-10) holding capacity for Clay 2, 3, 4, 6 and 7 is good and the performance of the remaining three is not bad. Results in Table 2 seem to indicate that the lower range of particles in the particle size distribution appear to have a positive contribution, due mainly to increased surface area, towards the oil holding capacity of the clay.

Improvements in the performance of the fabric in accordance with the invention is achievable by the use of surfactants such as described in British Patent No. 2,006,614. It is also possible to include fibrous material as disclosed in U.S. Pat. No. 4,100,324 by the means disclosed therein. Granular organic materials may also be incorporated and particles of cellulose sponge have been used as illustrated in FIG. 6. The water absorbent properties of the sponge contribute to the performance of the fabric as a water wipe. The sponge particle in FIG. 6 has a dimension of about 0.16 mm in one direction.

Fluid (Water & Oil) Holding Capacity of Clays
Fluid Holding Capacity (gram/gram)

| Clay No. | For Water Atmospheric Pressure | For Water Approx. 3 p.s.i. | For Oil (SAE-10) Atmospheric Pressure | For Oil (SAE-10) Approx. 3 p.s.i. | Particle Size Distribution (Microns) |
|---|---|---|---|---|---|
| 1. | 2.00 | 1.69 | 0.95 | 0.77 | +100 |
| 2. | 0.81 | 0.31 | 1.74 | 1.06 | ≅2–20 (<1 (20%)) |
| 3. | 0.31* | 0.22* | 1.98 | | (<2 (50%)) (>10 (10%)) |
| 4. | 0.32* | | 2.01 | 1.41 | |
| 5. | 1.16 | 1.03 | 0.95 | 0.84 | (<2 (15%)) (>10 (25%)) |
| 6. | 0.76 | 0.37 | 1.54 | 1.58 | (<2 (80%)) (>10 (60%)) |
| 7. | 0.72 | | 2.21 | 1.39 | (<2 (22%)) (>10 (28%)) |
| 8. | 0.66 | | 1.18 | 0.96 | (<2 (78%)) (>5 (0.5%)) |

1. The results in this table should only be considered for a relative comparison between the 8 different clays.
2. *Some of the fine particles were washed down with water through and along the sides of the Filter Paper No. 1.

TABLE 3

Rate of Wetting: Wickability
Basis: 10 gram of material (Clay)

| Sample No. | Rate (Seconds) | Colour | Moisture Content % |
|---|---|---|---|
| 1. | 13 | Brown | 2.1 |
| 2. | 240 | Off White | 0.8 |
| 5. | 350 | Pale | 2.2 |
| 4. | 152 | White | 0.4 |
| 5. (Lumps) | 724 | Pale | 14.4 |
| 6. | 345 | White | 1.1 |
| 7. | 240 | White | 0.3 |
| 8. | 585 | Off White | 0.4 |

Figure 7:
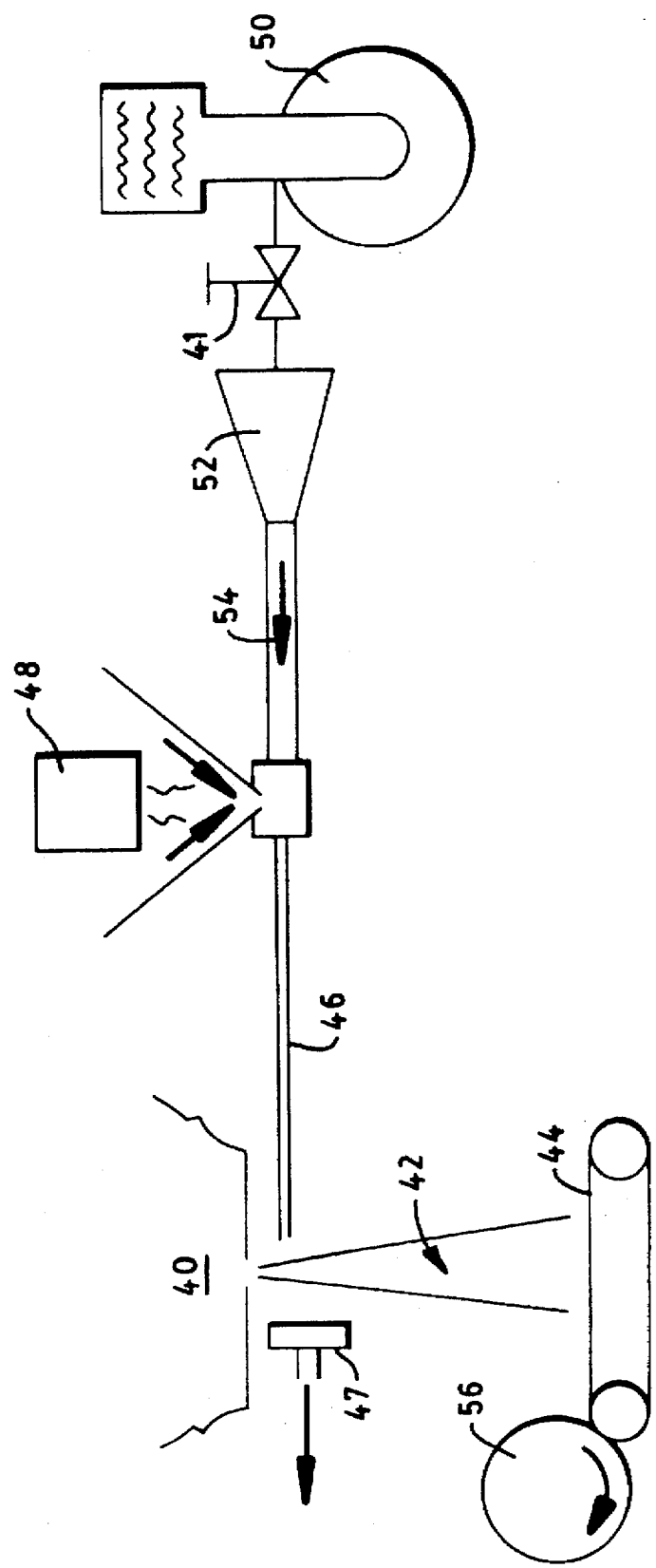
FIG. 7 is a diagrammatic illustration of an alternative apparatus for producing webs in accordance with the invention.

An alternative apparatus for use in producing a web in accordance with the invention and which is particularly suitable for the production of a web having particles of super absorbent material therein, is illustrated in FIG. 7.

The melt blown fibres are produced by a device similar to that illustrated in FIG. 1 and which is diagrammatically shown at 40 in FIG. 7. The stream 42 of fibres passes downwardly towards a screen collector 44 on which the fibres are consolidated into a web.

Particles of super asborbent material are blown onto the mat of melt blown fibres through a nozzle 46 shortly after the fibres leave the outlet nozzle of the melt blown extruder apparatus 40. The air stream has a velocity of about 6,000 feet per minute. This speed is adjusted by valve 41 so that the majority of the particles are just trapped by the melt blown fibres and do not pass through to the dust catcher 47. The speed may be adjusted according to the weight and size of the particles and may vary from say about 4,000 to say 7,000 feet per minute and dust is caught by a dust catcher 47.

The particulate super absorbent material is held in a particle dispenser 48 which may be that known as Model 500 made by the Oxi-Dry Corporation of Roselle, N.J., U.S.A., and is metered into an air stream formed by an air blower 50 passing through an air diffuser 52 and an air straightener 54. The powder in the dispenser is fed using an engraved metal roll in contact with two flexible blades. The cavity volume of the roll, roll speed and particle size control feed rate. An electrostatic charge is desirably applied to the particles to promote individual particle separation in the composite, as gravity drops the particles into the air stream.

High turbulence at the conversion of the separate air streams, one containing fibre and the other particulate super absorbent, results in thorough mixing and a high capture percentage of the particulates by the microfibre. The particles are thus distributed substantially individually and spaced throughout the web formed from the fibre/particle mix by collecting it on the moving screen 44. It is then wound, as a non-woven fabric, onto a roll 56.

As an example, polypropylene microfibre made from EXXON 3145 polypropylene resin from Exxon Chemical Company, Houston, Tex. was prepared in accordance with the procedure generally known as melt blowing. It is described in article "Super Fine Thermoplastic Fibres", appearing in INDUSTRIAL AND ENGINEERING CHEMISTRY, Volume 48, No. 8, Pages 1342 to 1346 and in U.S. Pat. Nos. 3,676,242 and 4,100,324.

A surfactant is applied to the microfibrous polypropylene at levels of 0.1 to 1.5 percent by weight to make the fibres wettable to aqueous solutions. In this Example, AEROSOL OT made by American Cyanamid Company, Wayne, N.J., was sprayed onto the fibres from dilute solution to an add on level of 0.27 percent by weight of fibre.

The powdered super absorbent used in this example was WATER-LOCK J-500 made by Grain Processing Corporation, Muscatine, Iowa.

Four separate sample composites were made having 2.4, 5.1, 8.1 and 13 percent by composite weight respectively of super absorbent.

Several tests of the samples were prepared as indicated below.

The first test performed was a saturated-capacity test. This test measures fluid holding capacity. Samples are cut, weighed, placed on a screen and submerged in a saline (0.85% Nacl) water bath for five minutes.

Saturated samples are removed from the bath and allowed to drain for two minutes. The sample is weighed and fluid weight absorbed is recorded as grams fluid per gram absorbent.

Fluid is then removed from the saturated sample using pressure applied with a vacuum box, a flexible rubber sheet and a screen support. Fluid retained after applying pressure for one minute is again measured by sample weights.

The second or horizontal wicking test measures distance of fluid migration as a function of time.

Sample strips 4 cm. wide by 50 cm. long were prepared and placed in a horizontal geometry on a plexiglass plate. A test fluid is put in a reservoir on one edge of the plate. One end of the samples are extended several centimeters off, the end of the plate and simultaneously pressed into the fluid. Distance wicked as a fraction of time is marked on the plate with ink and then recorded at the completion of each experiment.

A vertical wicking test on the samples was then performed. This test measures vertical distance wicked as a function of time.

Strips prepared as above are suspended vertically and the lower ends dipped into a fluid reservoir to a depth of 3.5 cm. Distance wicked above the fluid reservoir is recorded at specific time intervals.

Test Results

Figure 8:
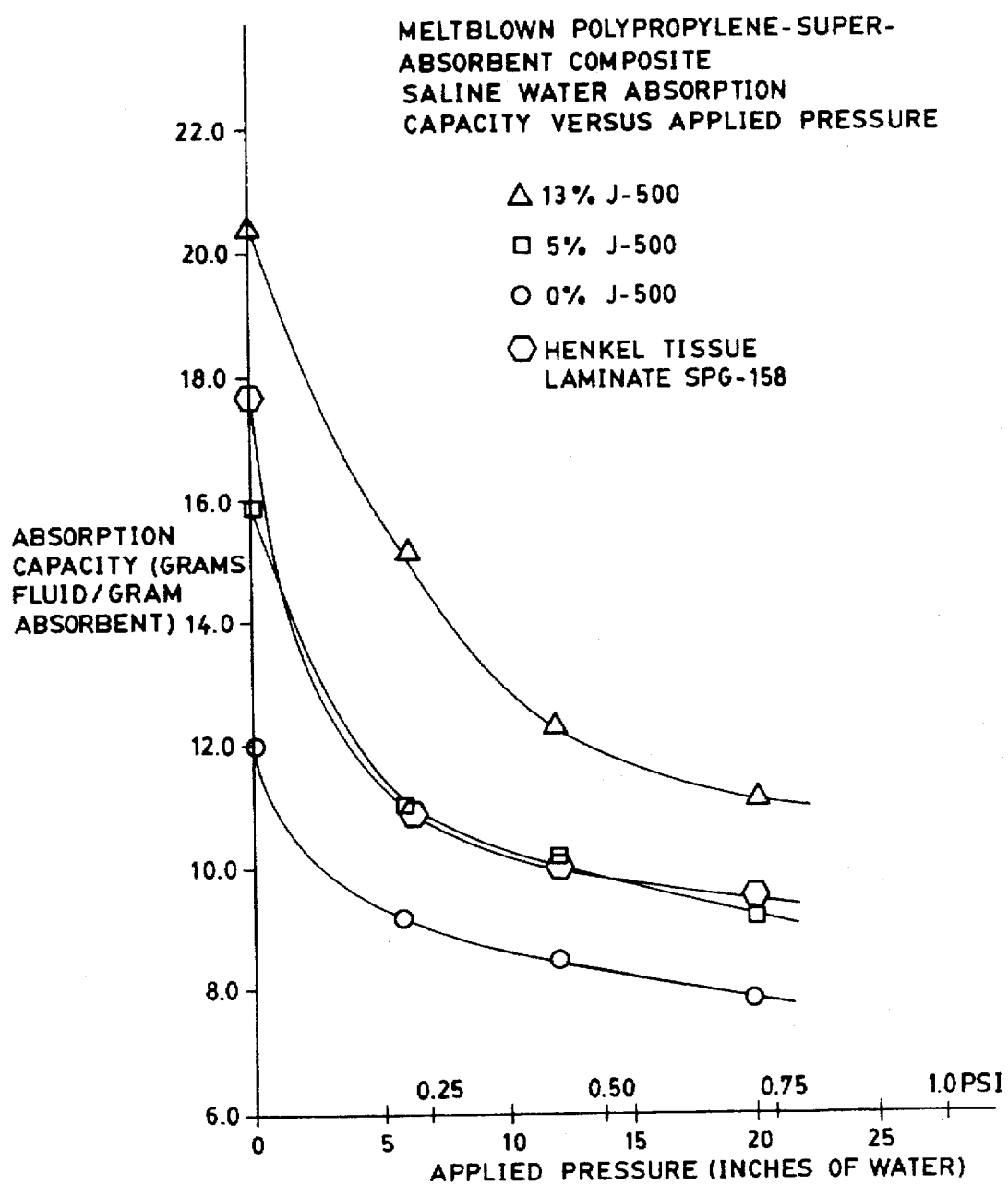
FIG. 8 is a graph comparing saturated capacity of super absorbent composites against a tissue laminated super absorbent versus applied pressure.

Saturated capacity of the microfibre super absorbent composites versus the microfibre control is shown in FIG. 8. At zero pressure the control microfibre absorbs 12 grams fluid/gram absorbent. With 13 percent super absorbent in the microfibre the absorption capacity is 20.4 grams fluid per gram of absorbent (showing a 70 percent increase in capacity). The fluid used in this example is dilute saline solution (0.85 percent by weight).

Results

For comparison, a tissue laminated super absorbent (SPG 157 from Henkel Chemical Co., Minneapolis, Minn., U.S.A.), are also shown in FIG. 8. Results show the tissue laminate capacity to be 17.5 grams fluid per gram absorbent at zero pressure. The 13 percent J-500 composite demonstrates a 16.6 percent saturated capacity increase over the tissue laminate.

As pressure is applied all the materials release some fluid. The capacity advantage of the composite is maintained to pressures of at least 0.75 pounds per square inch.

Figure 9:
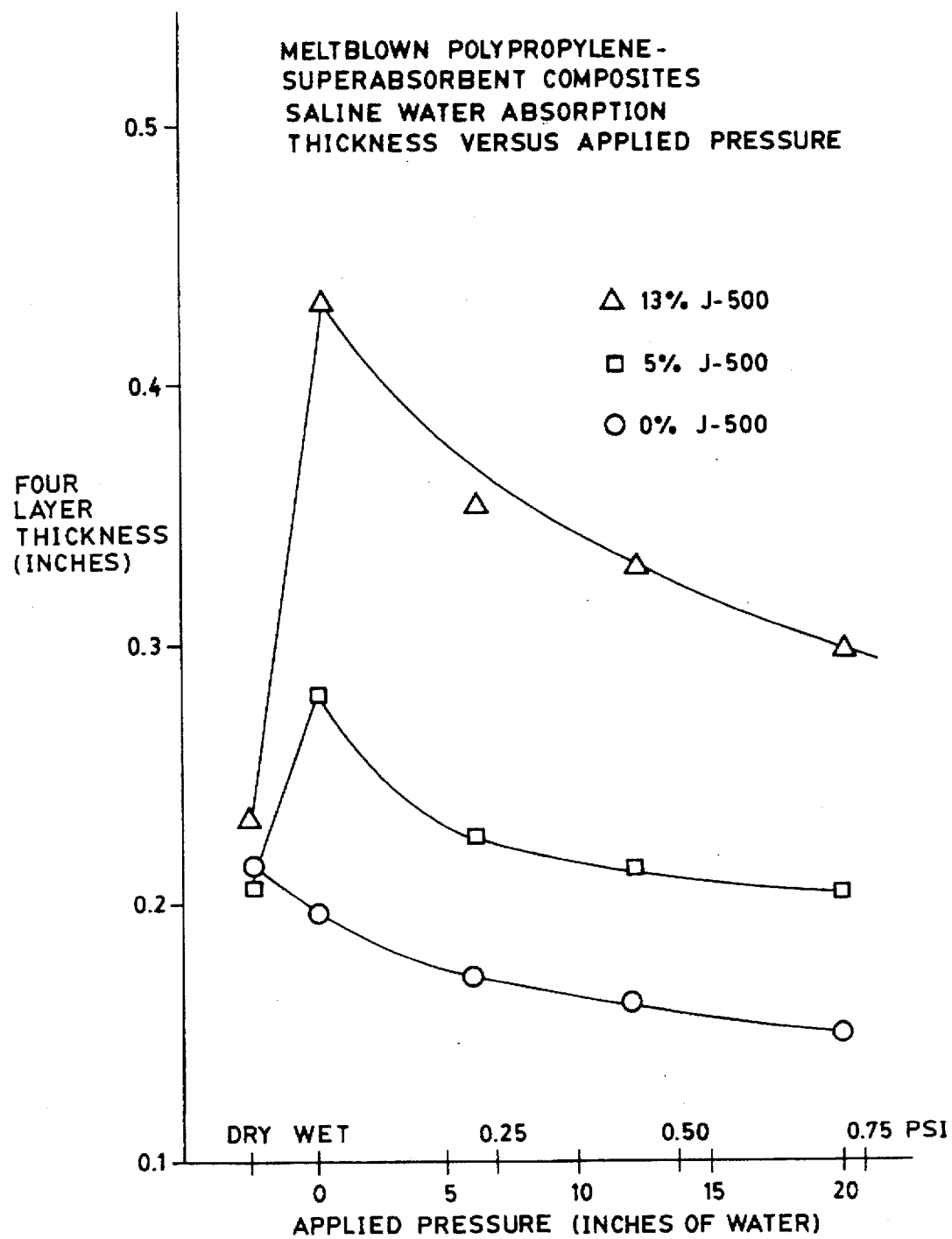
FIG. 9 is a graph showing the volume (thickness) of microfibre super absorbent composites versus applied pressure.
Figure 10:
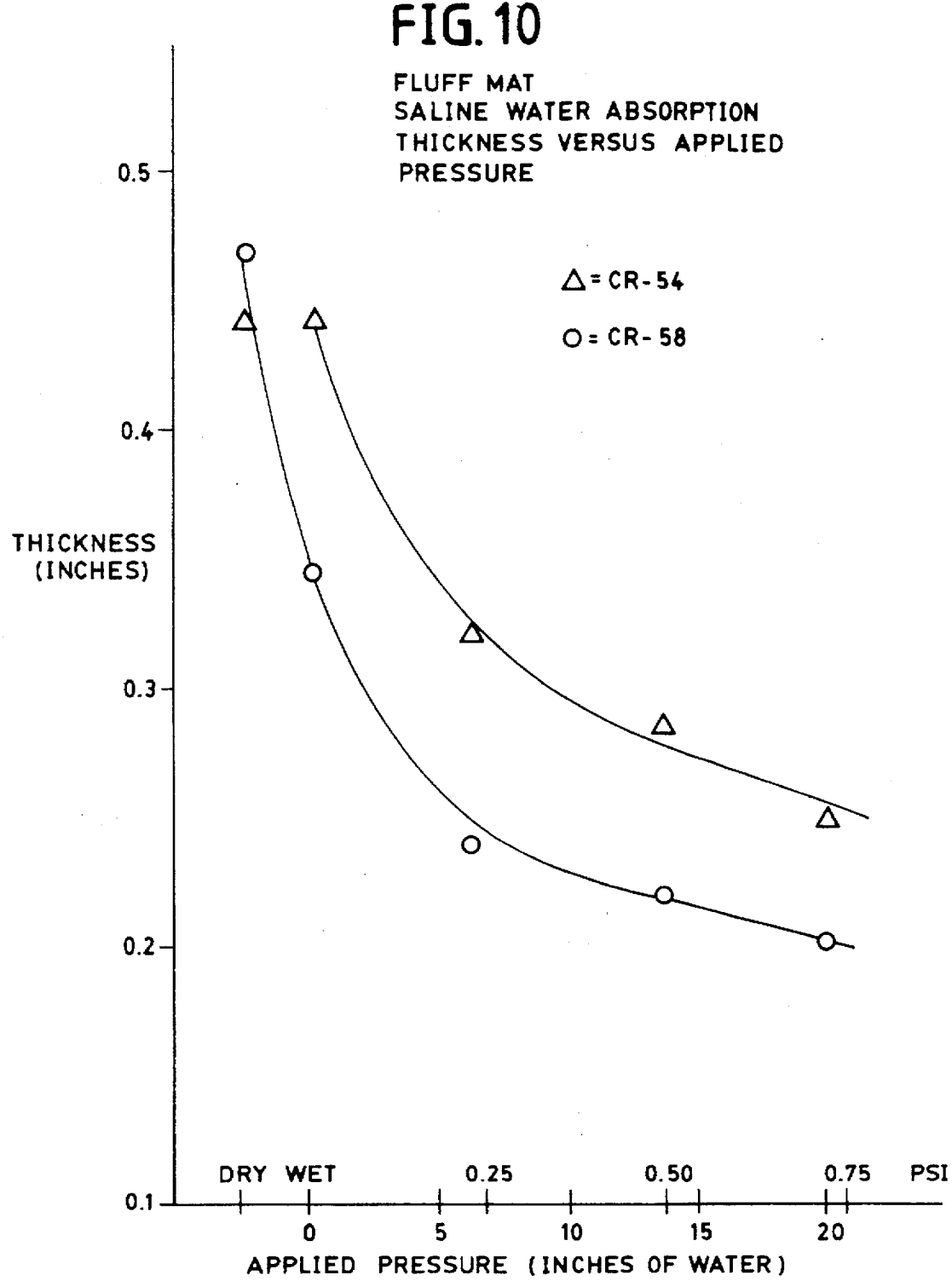
FIG. 10 is a graph showing the volume (thickness) of wood fluff absorbent versus applied pressure.

The volume (thickness) of the microfibre super absorbent composites is maintained better than microfibre and better than wood fluff absorbent (FIGS. 9 and 10). The super absorbent composites actually increase in volume as fluid is absorbed.

Figure 11:
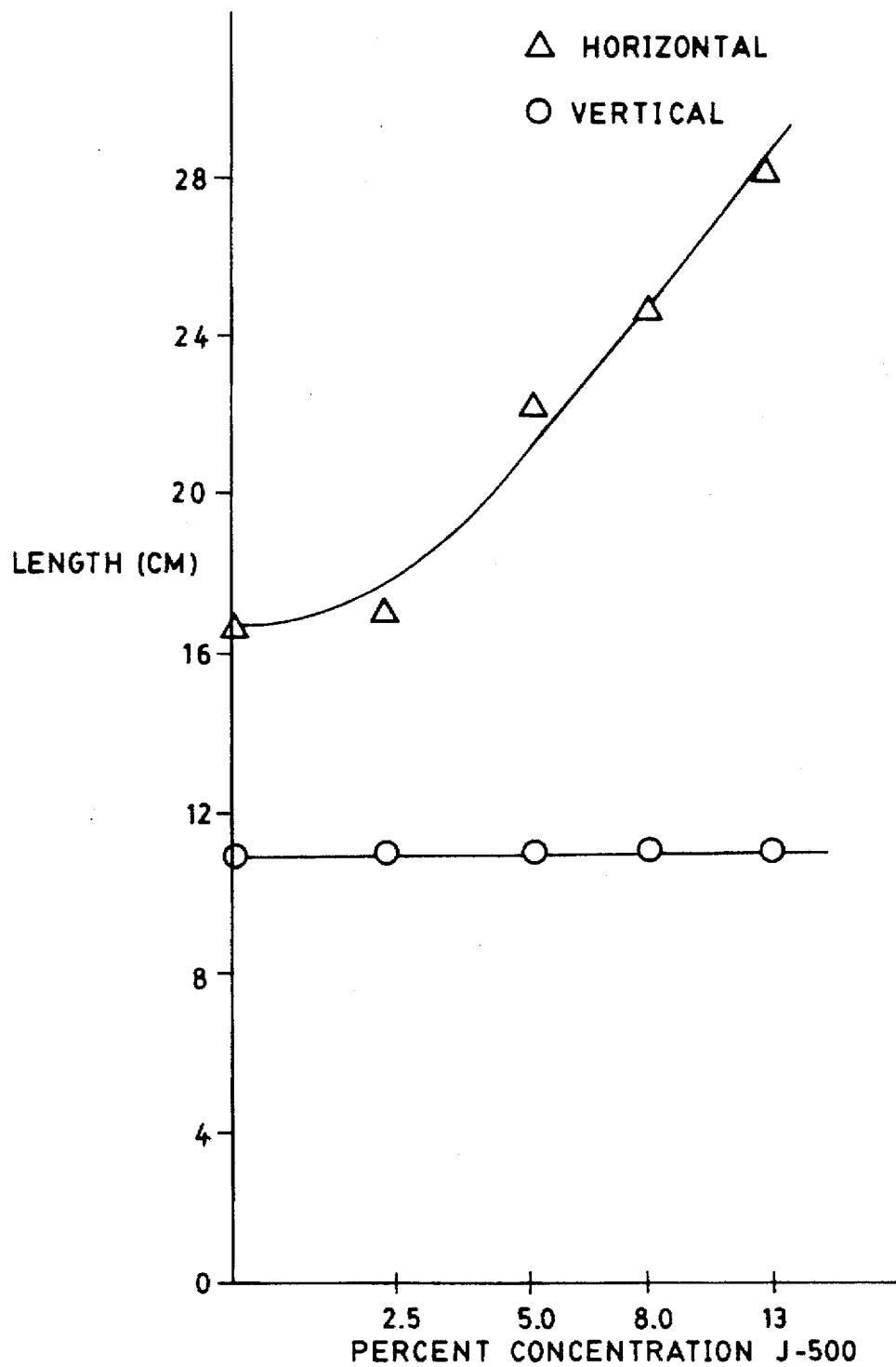
FIG. 11 is a graph showing the wickening of super asborbent composites versus percent concentration.

Horizontal wicking of the super absorbent composites versus an untreated microfibre control member (FIG. 11) show that the composites have better fluid transfer rates. Comparing horizontal wicking of the 13 percent J-500 composite to the Henkel laminated tissue SPG 157 shows the composite to wick 18.8 cm. after 600 seconds and the laminated tissue wicks 11.2 cm. This demonstrates a 67.9 percent increase in horizontal wicking for the composites over a commercially available product.

Vertical wicking shows that the superabsorbent composites have the same wicking properties as the microfibre control. No evidence of gel blocking is seen.

Comparing vertical wicking of 13 percent J-500 composite to the Henkel Laminated Tissue SPG-157 shows the composite to wick 11.1 cm., after 1300 seconds and the laminated tissue wicks 7.4 cm. This demonstrates a 50.0% increase in vertical wicking for the J-500 composite over a commercially available product.

Summary of Results

The microfibre composites containing Water-Lock J-500 absorbent shows improved absorbency characteristics of capacity and wicking over commercially available Henkel Laminated Tissue SPG-157 and also improvements over the currently produced microfibre without particle injected absorbents.

The particles of super absorbent material may have a relatively large diameter compared to the diameter of the individual microfibres and thus tend to be trapped within a network of the fibres and therefore little surface tack of the fibres is needed to maintain the super absorbent particles in place.

Figure 12:
FIG. 12 is an electron microscope photograph of fabric with super absorbent particles.

FIG. 12 is an electron microscope photograph of one example of web in accordance with the invention including particles 60 of super absorbent material. The photographs are of a sample having 17% by weight of super absorbent to fibre material and are to a magnification of one hundred and eighty times. The maximum particles dimensions of the particles illustrated are between 122×139 microns and 168× 213 microns and it can be seen that the particles are distributed substantially individually and spaced in the web sample.

We claim:

1. A method of making a meltblown nonwoven web containing absorbent particles comprising the sequential steps of:

a) forming a stream of molten and tacky polymeric fibers;

b) explicitly applying an electrostatic charge to said particles;

c) spacedly positioning and attaching absorbent particles to said fibers while said fibers are still tacky by introducing said charged particles into said stream; and d) forming a web by cooling and collecting said fibers.

2. A method according to claim 1 in which the absorbent particles are super-absorbent particles of modified starch or alginate.

3. A method as claimed in claim 1 in which the particles are blown onto the stream of fibers shortly after the fibers leave an extrusion nozzle.

4. A method as claimed in claim 1 in which a wetting agent is added to the fibers.

5. A method as claimed in claim 1 in which the particles are injected into an air stream prior to the air stream impinging on the fibers.

6. A method as claimed in claim 5 in which the velocity of said air stream is adjusted so that the majority of the particles are trapped by the melt blown fibers and do not pass through the fiber stream.

7. A method as claimed in claim 6 in which the said air stream has a velocity of about 6000 feet per minute.

8. A method as claimed in claim 1 in which the web is hot calendered or embossed by passing it between heated patterned bonding rolls.

9. A method as claimed in claim 8 in which the depth of the embossing member on the patterned roll is greater than the thickness of the web.

10. A method as claimed in either claims 8 or 9 in which the embossing rolls are driven at different speeds.

11. A method as claimed in claim 1 in which other fibers are introduced into the stream of microfibers prior to formation of the fibers into a web.

* * * * *